United States Patent [19]
Haynes

[11] Patent Number: 5,632,905
[45] Date of Patent: May 27, 1997

[54] METHOD AND APPARATUS FOR SEPARATING FORMED AND UNFORMED COMPONENTS

[76] Inventor: John L. Haynes, 20 Kendall Dr., Chapel Hill, N.C. 27514-5644

[21] Appl. No.: 512,123

[22] Filed: Aug. 7, 1995

[51] Int. Cl.⁶ ................................................ B01D 21/26
[52] U.S. Cl. .................. 210/782; 210/787; 210/789; 422/101; 422/102; 436/177; 446/46
[58] Field of Search ....................... 210/782, 516, 210/787, 789; 422/101, 102, 72, 73; 436/177; 273/424; 446/46

[56] References Cited

U.S. PATENT DOCUMENTS

| | | | |
|---|---|---|---|
| 3,113,396 | 12/1963 | Collins | 446/46 |
| 3,779,383 | 12/1973 | Ayres | 210/516 |
| 3,945,928 | 3/1976 | Ayres | 210/516 |
| 4,057,499 | 11/1977 | Buono | 210/136 |
| 4,979,922 | 12/1990 | Clark | 446/46 |
| 5,236,604 | 8/1993 | Fiehler | 210/782 |
| 5,271,852 | 12/1993 | Luoma, II | 210/516 |
| 5,277,641 | 1/1994 | Gable et al. | 446/46 |
| 5,366,403 | 11/1994 | Weiss | 446/46 |
| 5,454,958 | 10/1995 | Fiehler | 210/782 |

Primary Examiner—Robert J. Popovics

[57] ABSTRACT

A blood sample is gravimetrically separated into its heavier and lighter phases by centrifugation in a tube. The phases are separated by a disc which has a center of buoyancy and a center of mass that are spaced apart from each other along the axis of symmetry of the disc. The diameter of the disc is slightly larger than the bore diameter of the tube. The disc is initially positioned in the tube with its axis of symmetry perpendicular to the axis of the tube so that blood drawn into the tube can readily pass by the disc. Upon centrifugation, the disc will tumble through a 90° angle so that the axis of symmetry of the disc will be coincidental with the axis of the tube. Once the disc has tumbled in the sample, the ongoing centrifugal forces will cause a stretching of the disc along its axis of symmetry thereby decreasing the diameter of the disc. The stretching forces exerted on the disc will temporarily decrease the effective specific gravity of the disc so that the disc will remain in the upper portion of the lighter phase of the sample during the initial portion of the centrifugation. As the centrifuge slows down, the disc sinks through the lighter phase of the sample and settles on the interface between the lighter and heavier phases of the sample, thereby separating the two phases of the sample. One of the phases can then be removed from the tube without contamination from the other phase.

9 Claims, 1 Drawing Sheet

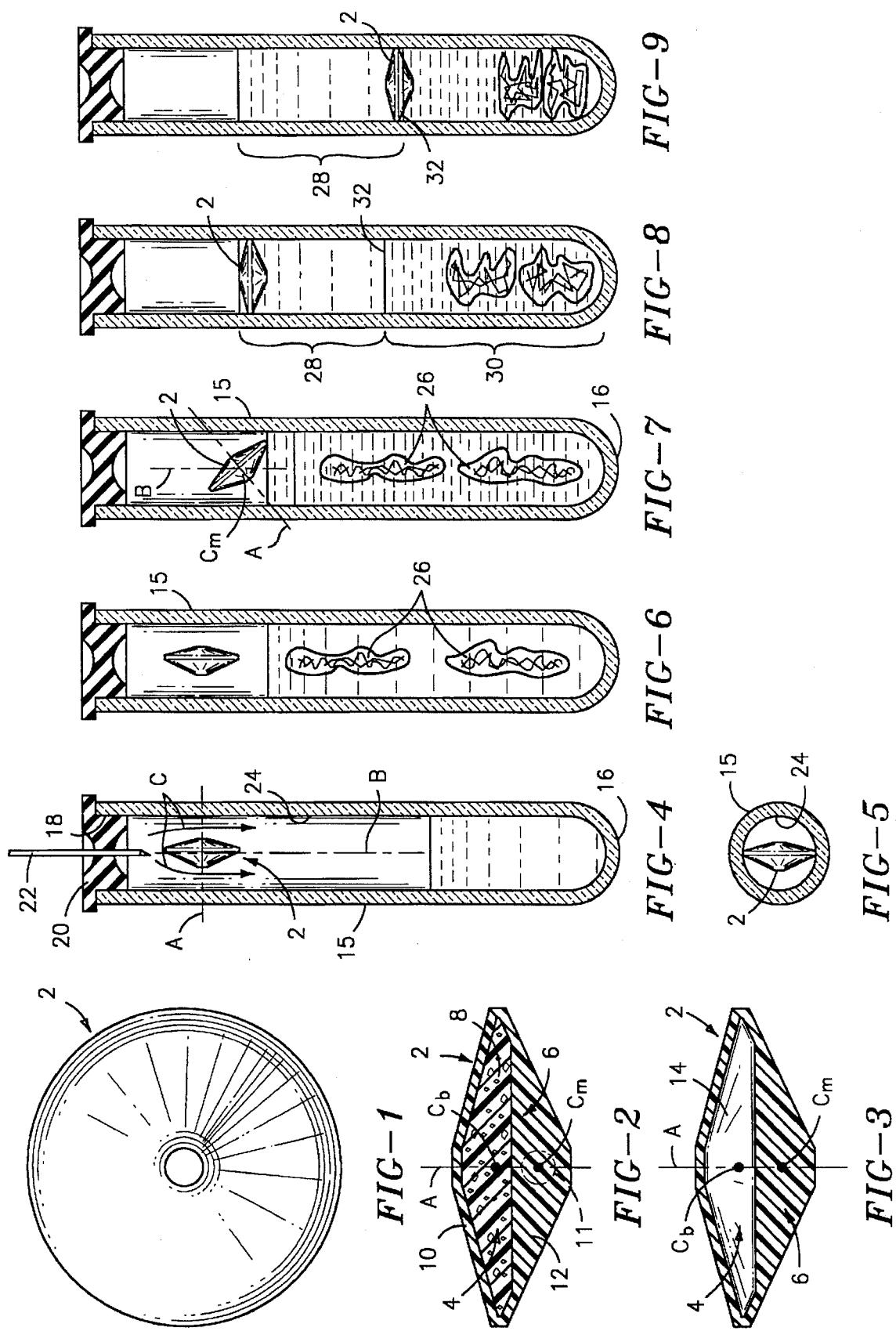

METHOD AND APPARATUS FOR SEPARATING FORMED AND UNFORMED COMPONENTS

TECHNICAL FIELD

This invention relates to an apparatus and method for separating formed components from unformed components, particularly, in a centrifuged sample of blood. The blood sample may be allowed to coagulate in the apparatus, or it may treated with an anticoagulant prior to the separation step.

BACKGROUND ART

It is well known to separate blood into its component parts by centrifugation, and to provide a barrier between the lighter liquid phase, e.g., the serum or plasma, and the heavier formed phase, e.g., the cells and/or fibrin, so as to physically separate the lighter phase from the heavier phase in the centrifuged blood sample. The blood to be tested may be collected in a blood collection container, and is thereafter centrifuged to separate the phases. In some cases, the barrier will be fixed in the tube, as shown in U.S. Pat. No. 3,945,928, and others; and in other cases the barrier will be movable in the tube during centrifugation, as shown in U.S. Pat. No. 5,271,852, and others. The barrier is typically a solid device, or a gel, In some cases the barrier may be positioned in the tube after the blood sample has been drawn, as shown in U.S. Pat. No. 4,057,499, for example; and in other cases the barrier may be positioned in the tube prior to drawing the blood sample, as shown in U.S. Pat. No. 3,779,383, among others.

There have been a great many solutions to the problem of how to separate the formed components from the unformed components in a centrifuged blood sample, but all suffer from various drawbacks. For example, it is undesirable to open the tube or perform any manipulations which might expose the operator to the blood sample, therefore it is highly desirable to have the barrier in the tube prior to drawing the blood sample. When a fixed barrier is used, care must be taken to locate the barrier in the tube in a position which will ensure that all of the formed component fraction of the blood sample will gravitate to a location that is below the fixed barrier during centrifugation. This frequently results in some of the non-formed component fraction also ending up beneath the barrier, and thus being lost to the clinician, a result which is undesirable.

When a solid barrier is preloaded into the tube prior to drawing the sample, there have been several approaches for solving the problem of how to separate the solid phase from the liquid phase in the blood sample by centrifugation, it being obvious that one must be able to get the solid phase components, i.e., essentially the cells, past the solid barrier. One solution suggested in the prior art is to provide the solid barrier with a flexible skirt which partially collapses during the centrifugation so as to allow the solid phase and liquid phase fractions to pass by the exterior of the barrier. Another solution is to place the solid barrier on the bottom of the tube prior to drawing the sample into the tube. In this case, the barrier may include an internal opening which acts as a check valve through which the heavier phase is intended to pass during centrifugation so as to lift the barrier to a location in the tube which is between the heavier and lighter phases of the centrifuged sample. Alternatively, the barrier may include an outer part which will contract when subjected to the pressure developed in the sample during centrifugation. The heavier phase is intended to gravitate around the barrier so as to lift the barrier to the proper location in the tube. These solutions are relatively complex, and are not readily usable with clotted blood because the clots cannot readily bypass the solid barrier in the tube during centrifugation.

The separating barrier must be inert, i.e., it must not add to or subtract from the chemistry of the serum/plasma phase. One problem encountered with gel barrier materials is that they may absorb some sample additives, e.g., therapeutic drugs or other additives placed in the tube and necessary for proper sample analysis; and also may also spawn or generate gel particles which can clog instruments used to analyze the serum/plasma phase.

It would be highly desirable to provide a solid, inert barrier which can be preloaded into a blood drawing tube; which will not interfere with drawing of the blood sample; and which will settle onto the heavy phase-lighter phase interface during centrifugation of the sample. It would be highly desirable to provide such a barrier member which can be used with both anti coagulated, and non-anti coagulated blood samples.

DISCLOSURE OF THE INVENTION

This invention is directed to a phase separation assembly for use in separating lighter and heavier phase fractions of a multi-phase material, such as blood. The assembly includes a solid, inert plastic separator or barrier which is essentially disc-shaped. The separator disc is formulated so as to have a center of mass ($C_m$) and a center of buoyancy ($C_b$) which are spaced apart from each other along the axis of symmetry of the separator disc. It will be noted that the specific gravity of the $C_b$ side of the disc will be less than the specific gravity of the $C_m$ side of the disc. The disc is placed in the evacuated collection tube with its axis of symmetry essentially perpendicular to the axis of the tube. When the separator disc is thus positioned in the tube, blood flowing into the tube can readily stream past the disc and fill the tube to the extent necessary. The collection tube is preferably a pre-evacuated tube with a rubber stopper that is pierced by a needle cannula, and which reseals itself when the cannula is withdrawn. After the blood sample is drawn into the tube, when the sample has not been treated with an anticoagulant, the sample will be allowed to sit for a time needed to form the desired extent of clotting in the tube before centrifugation. If the blood sample has been treated with an anticoagulant, the sample will be immediately ready to centrifuge.

The high speed centrifugation of the sample causes the disc to tumble through a 90° angle so that the $C_m$ side of the disc faces the lower closed end of the sampling tube, and the $C_b$ side of the disc faces the stoppered end of the tube. During the high speed centrifugation, the two parts of the disc are pulled in opposite directions by the forces of centrifugation, increasing its volume, so as to lower the average specific gravity of the disc to the extent necessary to cause the disc to float on or near the top of the lighter phase of the blood sample until the centrifuge slows down. At the conclusion of centrifugation, the phase separation disc will settle into the interface between the lighter and heavier phases and form a seal between the two phases.

It is therefore an object of this invention to provide a novel barrier generally in the form of a disc which is operable during centrifugation to physically separate lighter and heavier phases of a mult-phase centrifuged material, such as blood.

It is a further object of this invention to provide a barrier of the character described which has opposed sides, one side having a specific gravity which is less than the specific gravity of the heavier phase of the material, and the other side having a specific gravity which is approximately equal to the specific gravity of the heavier phase.

It is another object of this invention to provide a barrier of the character described which cannot exude oils or particles which could clog sensitive instruments.

It is an additional object of this invention to provide a barrier which is adapted for use with both anti coagulated and clotted blood samples.

It is yet another object of the invention to provide a barrier which remains above the heavier phase of the blood sample until the phase separation is complete and the centrifuge slows.

It is a further object of the invention to provide a barrier which radially contracts during centrifugation to allow the heavier phase of the blood sample to bypass the barrier until separation is complete and the centrifuge slows.

These and other objects and advantages of the invention will become more readily apparent from the following detailed description of several embodiments of the invention when taken in conjunction with the accompanying drawings in which:

BRIEF DESCRIPTION OF THE DRAWINGS

FIG. 1 is a plan view of separator disc designed for use in connection with this invention;

FIG. 2 is an axial sectional view of one embodiment of the disc shown in FIG. 1;

FIG. 3 is a view similar to FIG. 2 but showing a second embodiment of the disc;

FIG. 4 is sectional view of an assembly for collecting blood and centrifugationally separating the blood into its heavier and lighter phases in accordance with this invention;

FIG. 5 is a cross sectional view of the tube showing the initial position of the separator disc in the tube prior to centrifugation;

FIG. 6 is a view similar to FIG. 4, but showing the blood as it begins to clot in the sampling assembly;

FIG. 7 is a view similar to FIGS. 4 and 6 but showing the separator disc as it begins to tumble toward its sealing position during centrifugation of the sample in the tube;

FIG. 8 is a view similar to FIG. 7 but showing the separator disc after it tumbles into its sealing position and while it floats in the lighter phase of the sample during continued centrifugation of the sample in the tube; and FIG. 9 is a view similar to FIG. 8 but showing the separator disc after it has settled into its sealing position upon completion of centrifugation of the sample in the tube.

DETAILED DESCRIPTION OF SPECIFIC EMBODIMENTS OF THE INVENTION

Referring now to the drawings, there is shown in FIGS. 1–3 a disc-shaped separator barrier which is denoted generally by the numeral 2. As seen in FIGS. 2 and 3, the barrier disc 2 is thickest at its axis of symmetry A, and it thins toward its circumference, and it has two points, $C_m$ and $C_b$, which are, respectively, the center of mass, and the center of buoyancy of the disc 2. The disc 2 takes advantage of two well known physical principles: a) that gravitational forces influencing a body, act as if the gravitional forces were imposed on the body solely at the center of mass; and b) buoyancy forces influencing a body which is immersed in a fluid act as if the buoyancy forces were imposed on the body solely at the center of buoyancy. The disc 2, as shown in FIGS. 1–3, comprises a first portion 4 which is formed from a material having a specific gravity that is less than the specific gravity of the material from which the portion 6 is formed. This results in the center of mass $C_m$ being spaced apart, or offset, from the center of buoyancy $C_b$, along the axis of symmetry A of the disc.

FIG. 2 shows a separator disc 2 wherein the $C_b$ is contained in a lower specific gravity substance, which may be, for example, a foamed plastic material 8 having an outer skin 10. The foam core 8 has a lower specific gravity than the opposite side 12 which may be formed as a solid piece of the skin material 10. The $C_m$ will be located inside of the solid half 12 of the disc 2, as shown in FIG. 2. The $C_b$ and the $C_m$ will thus be spaced apart from each and each will be located essentially on the axis of symmetry A of the disc 2. The disc 2 may also be formed with an encapsulated insert made from a heavier material, such as a metal pellet, which is shown in phantom in FIG. 2, and is designated by the numeral 11, on the $C_m$ side of the disc 2.

FIG. 3 shows an alternate embodiment of the separator disc 2, wherein the $C_b$ side of the disc 2 will be filled with air or some other suitable gas, as indicated at 14. The use of a hollow $C_b$ side of the disc 2 allows the use of a heavier range of materials for the $C_m$ side of the disc 2 while maintaining the required average density for the disc 2 over all. The use of a gas has several advantages. It provides the greatest possible difference in specific gravity between the opposite portions of the disc 2, thereby imparting to the disc 2 the greatest tumbling impulse possible to achieve the results described hereinafter. It also provides an buoyant portion which is more easily distorted during the stretching action which occurs in the disc 2 during centrifugation. It also allows the use of a single material in manufacture and in qualification for biocompatibility with the blood sample.

Referring now to FIGS. 4–9 there is shown a transparent blood collection tube 15 which is preferably formed from glass or plastic, and which is closed at one end by an integral wall 16. The tube 15 has an opposite open end 18 that is preferably sealed by an elastomeric stopper 20. The stopper 20 is pierced by a blood drawing needle 22 and the stopper 20 is self-sealing after being pierced. The collection tube 15 is provided with a predetermined negative pressure, or partial vacuum, that is maintained by the stopper 20, so that the blood will flow readily into the tube 15, as indicated by the arrows C in FIG. 4. As seen in FIGS. 4–6, the disc 2 is predisposed in the tube 15 with its axis of symmetry A oriented perpendicular to the axis B of the tube 15. The diameter of the disc 2, when in a static situation, is slightly larger that the diameter of tube bore 24, so that the disc 2 will remain in the position shown in FIGS. 4–6 during ordinary handling of the tube 15, held in place in the tube bore 24 by the slight compression of the separation disc 2. In this regard, the disc 2 acts in the manner of a butterfly valve, the disc 2 (valve) being shown in its open position in FIGS. 4–6.

Referring now to FIG. 6, the drawn blood is shown at rest and forming clots 26, which is desirable for a blood sample from which serum is to be harvested. When necessary, or desired, clot activation additives can be added to the tube 15. In the event that plasma is desired, an anti-coagulant, such as EDTA, can be added to the tube 15 to prevent the formation of clots 26 in the blood sample. In such cases, the blood sample can be centrifuged immediately after drawing the sample.

After the blood sample is drawn, and any necessary clotting takes place, the filled tube 15 is placed in a centrifuge (not shown) with the closed end 16 of the tube 15 being disposed radially outwardly of the axis of the centrifuge, and the tube 15 is centrifuged at rates which will result in peak forces ranging from 800 times the force of gravity (800 G) to over 5,000 times the force of gravity (5,000 G) being imposed on the contents of the tube 15. This centrifugation step continues for a time sufficient to gravimetrically separate the heavy phase of the sample from the lighter phase.

Referring now to FIG. 7–9, it will be noted that clots 26, if any are present, or red cells, will gravitate toward the closed end 16 of the tube 15, since they have a greater specific gravity than the serum or plasma phase. FIG. 7 also shows that the separation disc 2 will gravitate and begin to tumble toward the closed end 16 of the tube 15 under the influence of the forces of centrifugation, thereby overcoming the frictional forces previously holding the disc 2 in place in the tube 15. As the disc 2 is displaced, it also rotates in a direction that will position the $C_m$ side of the disc 2 closer to the closed end 16 of the tube 15, so that the axis of symmetry A of the disc 2 will begin to align with the axis B of the tube 15.

FIG. 8 shows the position of the disc 2 when separation of the lighter phase 28 from the heavier phase 30 in the blood sample has been achieved. At this point in the centrifugation, the disc 2 will have tumbled through the 90° angle in the tube 15 so that the axis of symmetry A of the disc 2 coincides with the axis B of the tube 15. It will be noted that the disc 2 will begin to sink through the lighter phase 28 toward the interface 32 with the heavier phase 30. The reason that substantial movement of the disc 2 toward the interface 32 does not begin until separation has been substantially completed is that the disc 2 will stretch under the higher G forces during centrifugation, and its effective overall specific gravity will decline due to the enhanced buoyancy of the $C_b$ side of the disc 2. Once the centrifuge begins to slow down, the disc 2 will relax and the buoyancy effect of the $C_b$ side of the disc 2 will decline so as to increase the effective overall specific gravity of the disc 2. Once this occurs, the disc 2 (along with formed elements) will descend through the lighter phase 28 in the centrifuged blood sample. When the centrifuge has stopped, the disc 2 will have settled onto the interface 32, as shown in FIG. 9. It should be noted that the stretching force imposed on the disc 2 while the centrifuge is still operating will effectively reduce the diameter of the disc 2 so as to facilitate its descent through the lighter phase 28 in the sample. At rest, it is necessary that the average specific gravity of the disc 2 be about 1.06 so as to be intermediate the specific gravities of the two blood phases so that the disc 2 will settle onto the sample interface 32 when the separation step is completed.

It will be understood that the different specific gravities of the opposite sides of the disc effectively moves the center of mass of the disc below the center of buoyancy thereof, and also below the plane of maximum diameter of the disc. This results in important and novel consequences when the disc is subjected to the high gravitational forces of a centrifuge. For example, the differential specific gravity provides the forces required to tumble the disc. Additionally, the differential specific gravity provides a stretching force along the axis of symmetry of the disc when the disc is subjected to the centrifugal pull, which stretching force is operable to reduce the circumference of the disc thereby allowing the disc to sink through the lighter phase of the centrifuged sample toward the interface with the heavier phase. This stretching force also reduces the average specific gravity of the disc while the centrifuge is at full speed, permitting the disc to float at or near the top of the lighter phase while phase separation is in process. Examples of materials which may be used for the $C_b$ portion of the disc are soft elastomers such as Santoprene™ or Kraton™ which are trademarks for relatively low specific gravity plastics sold by Monsanto and Shell respectively, and which have specific gravities in the range of 0.9 to 1.0. Examples of materials which may be used for the $C_m$ portion are rubbers or plastics, of a specific gravity ranging from 1.1 to 2.0 which will result in the desired average specific gravity of 1.04 to 1.07 for the complete disc.

Since many changes and variations of the disclosed embodiment of the invention may be made without departing from the inventive concept, it is not intended to limit the invention otherwise than as required by the appended claims.

What is claimed is:

1. A separator body for separating a formed phase from an unformed phase in a centrifuged sample of a multi-phase material in a test tube, said separator body being sized to fit snugly in said test tube and being generally disc-shaped and having an axis of symmetry which is disposed perpendicular to its circumference, and said separator body having a center of mass (Cm) and a center of buoyancy (Cb) which are spaced apart from each along said axis of symmetry of the body so as to impart to the body a first side having a higher specific gravity, and a second opposite side having a lower specific gravity.

2. The separator body of claim 1 wherein said first side is formed from a higher specific gravity plastic material, and said second side is formed from a lower specific gravity plastic material.

3. The separator body of claim 2 wherein said first side is formed from a solid plastic material, and said second side is formed from a foamed plastic material.

4. The separator body of claim 3 wherein said second side is formed with a solid plastic skin covering said foamed plastic material.

5. An assembly for gravimetrically separating a formed phase from an unformed phase in a centrifuged sample of a mult-phase material, said assembly including:
   a) a tube for holding the material sample, said tube having a bore and an axis; and
   b) a separator body disposed in said tube, said separator body being generally disc-shaped and having an axis of symmetry which is disposed perpendicular to its circumference, and said separator body having a center of mass ($C_m$) and a center of buoyancy ($C_b$) which are spaced apart from each along said axis of symmetry of the body so as to impart to the body a first side having a higher specific gravity, and a second opposite side having a lower specific gravity, and said separator body being positioned in said tube with its axis of symmetry disposed at essentially right angles to the axis of said tube, and with its circumference being wedged against opposite sides of the tube bore so as to provide minimal interference with flow of the material into said tube.

6. A method for gravimetrically separating a formed phase from an unformed phase in a centrifuged sample of a mult-phase material in an assembly which comprises a tube having a bore with an axis of elongation, a generally disc-shaped separator body having an axis of symmetry which is disposed perpendicular to its circumference and having a center of mass (Cm) and a center of buoyancy (Cb) which are spaced apart from each along said axis of symmetry so as to impart to the body a first side having a higher specific gravity, and a second opposite side having a lower specific gravity, which body is positioned in said tube bore with the axis of symmetry of said body being disposed at essentially a 90° angle relative to the axis of elongation of the tube bore so as to open the tube bore for admission of the sample into the tube, said method comprising the steps of:

a) drawing the sample of the multi-phase material into the tube;
   b) centrifuging the multi-phase material sample at G forces which will separate the formed phase from the unformed phase and will cause the separator body to tumble in the tube to a barrier position wherein the axis of symmetry of the separator body coincides with the axis of elongation of the tube bore; and
   c) causing the separator body to gravitate onto an interface between the formed and unformed phases of the material sample during said centrifuging step so as to form a barrier between the formed and unformed phases in the sample.

7. An assembly for gravimetrically separating a heavier phase from a lighter phase phase in a centrifuged sample of a multi-phase material, said assembly including:

a) a tube for holding the material sample, said tube having a bore and an axis of elongation; and
   b) a separator body disposed in said tube, said separator body being disposed in a first position wherein its center of mass is laterally spaced apart from said axis of elongation of said tube, said separator body having a circumferential surface which is wedged against opposite sides of the tube bore so as to provide minimal interference with flow of the material into said tube when in said first position, and said circumferential surface providing a pivot axis which allows the separator body to reorient during centrifugation of the sample in the tube to a second position wherein said center of mass is positioned on said axis of elongation of the tube, said separator body being operable to separate heavier and lighter phases of said sample when in said second position.

8. A method for gravimetrically separating a heavier phase from a lighter phase in a centrifuged multi-phase material in an assembly which comprises a tube having a bore with an axis of elongation; and a separator body having a center of mass, said separator body being positioned in said tube bore in a first position wherein the center of mass of said body is disposed radially offset from the axis of elongation of the tube bore and wherein said separator body is oriented relative to the tube bore axis so as to open the tube bore for admission of the sample into the tube, said method comprising the steps of:

a) drawing a sample of the multi-phase material into the tube;
   b) centrifuging the multi-phase material sample at G forces which will separate the heavier phase from the lighter phase and will cause the separator body to reorient in the tube to a barrier position wherein the center of mass of the separator body coincides with the axis of elongation of the tube bore; and
   c) causing the separator body to gravitate onto an interface between the heavier and lighter phases of the material sample during said centrifuging step so as to form a barrier between the heavier and lighter phases in the sample.

9. A method for gravimetrically separating a heavier phase from a lighter phase in a centrifuged multi-phase material in an assembly which comprises a tube having a bore with an axis of elongation; and a separator body having a center of mass, said separator body being positioned in said tube bore in a first position wherein the center of mass of said body is disposed radially offset from the axis of elongation of the tube bore and wherein said separator body is oriented relative to the tube bore axis so as to open the tube bore for admission of the sample into the tube, said method comprising the steps of:

a) drawing a sample of the multi-phase material into the tube;
   b) centrifuging the multi-phase material sample at G forces which will separate the heavier phase from the lighter phase and will cause the separator body to reorient in the tube to a barrier position wherein the center of mass of the separator body coincides with a centrifugal force vector line created in the tube by said centrifuging step; and
   c) causing the separator body to gravitate onto an interface between the heavier and lighter phases of the material sample during said centrifuging step so as to form a barrier between the heavier and lighter phases in the sample.

* * * * *